United States Patent [19]

Inoue et al.

[11] Patent Number: 4,613,688

[45] Date of Patent: Sep. 23, 1986

[54] OPTICAL RESOLUTION PROCESS FOR DL-CYSTEINE

[75] Inventors: Chozo Inoue, Kanagawa; Yoshiko Kurima; Soyao Moriguchi, both of Tokyo, all of Japan

[73] Assignee: Showa Denko Kabushiki Kaisha, Tokyo, Japan

[21] Appl. No.: 364,702

[22] Filed: Apr. 2, 1982

[51] Int. Cl.$^4$ .............................................. C07B 57/00
[52] U.S. Cl. .................................... 562/401; 562/402; 562/436
[58] Field of Search ................................ 562/401, 402

[56] References Cited

U.S. PATENT DOCUMENTS 2,898,358  8/1959  Dowling ......................... 562/402 X Primary Examiner—Natalie Trousof
Assistant Examiner—Vera C. Clarke
Attorney, Agent, or Firm—Sughrue, Mion, Zinn, Macpeak & Seas

[57] ABSTRACT

A process for the optical resolution of DL-cysteine which comprises (1) converting DL-cysteine into a hydrochloride thereof and forming a saturated or supersaturated aqueous solution thereof, (2) inoculating the solution with crystals of one optically active form of cysteine hydrochloride as seed crystals, and (3) preferentially crystallizing optically the same form of the cysteine hydrochloride used as the seed crystals, in a state of a monohydrate thereof.

5 Claims, 1 Drawing Figure

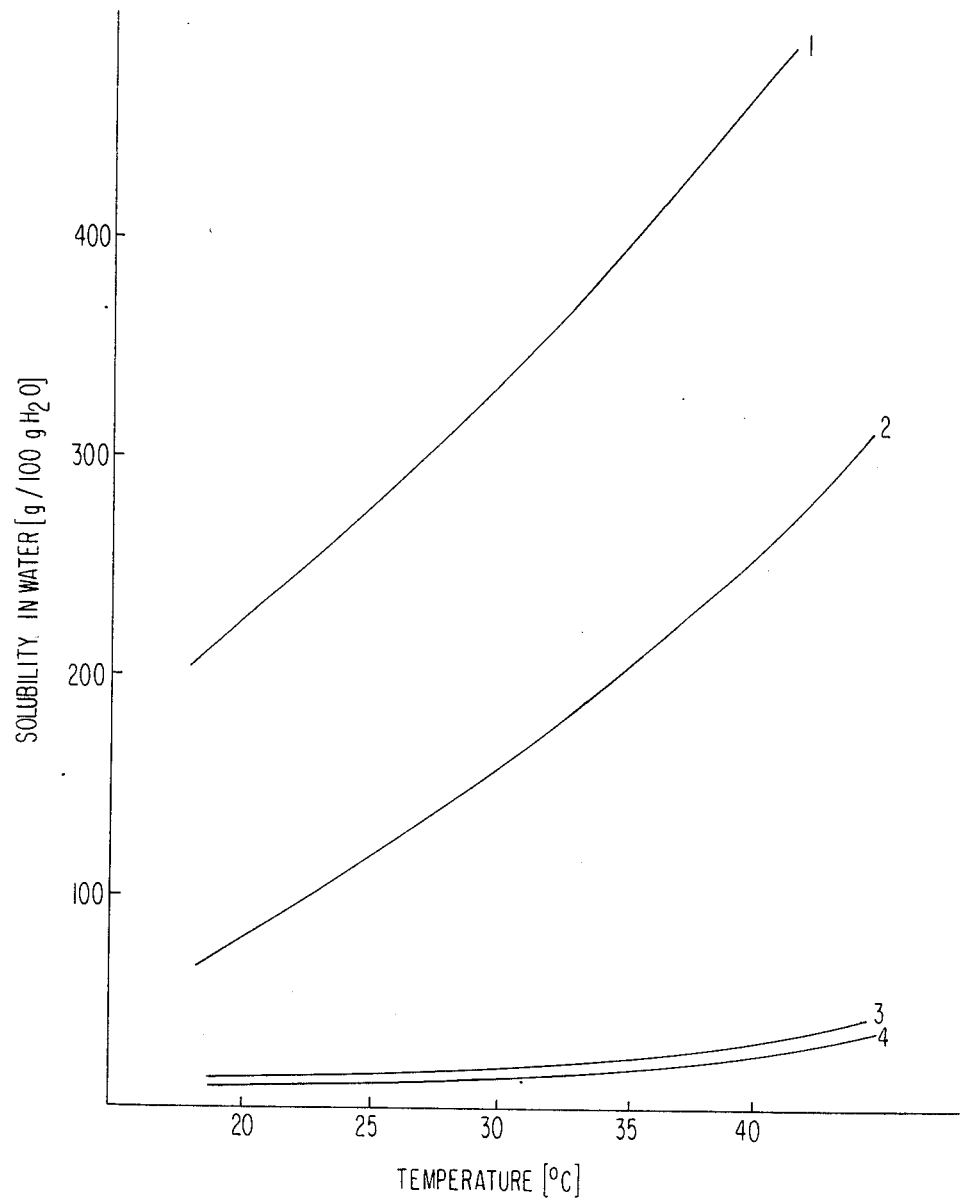

OPTICAL RESOLUTION PROCESS FOR DL-CYSTEINE

FIELD OF THE INVENTION

The present invention relates to a process for the optical resolution of DL-cysteine and, particularly, to a process for preferentially preparing L- (or D-) cysteine hydrochloride by optical resolution of DL-cysteine hydrochloride after converting DL-cysteine into a hydrochloride thereof and carrying out fractional crystallization thereof or simultaneously crystallizing crystals of both optically active forms.

BACKGROUND OF THE INVENTION

Cysteine is a sulfur containing amino acid, which includes three forms—the optically active D-form, the optically active L-form and the optically inactive DL-form (racemate) which is an equivalent weight mixture of the D-form and the L-form. At present, L-cysteine is a predominant product, because it is industrially produced by extraction from hydrolyzates of natural materials (for example, hair and wool, etc.), and it has been used for producing medicines, food additives, cosmetics and feed stuffs, etc. However, there is a problem in that the supply of the raw material is unstable because it is obtained from natural materials. Thus, various processes for synthesizing it by chemical means using chemicals readily available as raw materials have been studied. However, when known processes are utilized, optical resolution must be carried out in order to obtain only the L-form, because the form of cysteine synthesized by chemical means is the DL-form. On the other hand, recently, D-cysteine has been discovered to have a medical effect, but this form is difficult to find in natural materials. Thus, no suitable process is known for obtaining this form, except a process which comprises racemizing the L-form obtained from natural materials such as those described above to form the DL-form or synthesizing the DL-form by chemical means, and carrying out an optical resolution.

Generally various processes such as a physicochemical process, a chemical process, a biological process or an enzymatic process, etc., are known for the optical resolution of racemic organic compounds. Many approaches, including those for glutamic acid, have been developed in case of amino acids. In the optical resolution processes used hitherto, the most industrially advantageous process is believed to be the so-called inoculation crystallization process which is capable of preferentially crystallizing the L-form or the D-form from an aqueous solution of the racemate. However, resolution of many amino acids cannot be carried out by the inoculation crystallization process, because the DL-form thereof forms a molecular compound. Therefore, the production of crystal forms from which resolution can be carried out has been sought, for example, by conversion into salts of organic or inorganic acids, metal salts, N-acylated derivatives and so on of the amino acids. However, the ability to predict the formation of crystals from which resolution can be carried out for individual amino acids has not been developed yet. Accordingly, under present conditions, crystal forms from which resolution can be carried out are basically determined empirically as a result of many experiments.

With respect to cysteine, some reports exist on chemical processes, for example, a process which comprises converting cysteine into an N-acyl-S-benzyl derivative, adding thereto an optically active agent for resolution and carrying out the resolution by utilizing the difference in solubilities of the formed diastereomers. However, a process for physicochemically carrying out the optical resolution of cysteine directly is not known. Namely, not only does cysteine have a comparatively low solubility in a neutral aqueous solution but it is easily oxidized by dissolved oxygen to form cystine. Particularly, oxidation of cysteine is remarkably accelerated when a very small amount of metal ions such as iron or copper is present. Further, because DL-cysteine forms a molecular compound and has a slightly lower solubility in water than the L-form (or the D-form) [in attached FIGURE, curves ④ and ③ show the solubility in water of DL-cysteine (racemate) and the L-form or D-form of cysteine, respectively], it is impossible for resolution to be carried out by inoculation.

SUMMARY OF THE INVENTION

As a result of extensive research on an advantageous process for industrially carrying out the optical resolution of cysteine, the process of the present invention has been completed.

The present invention provides a process for the optical resolution of DL-cysteine which comprises
(1) converting DL-cysteine into a hydrochloride thereof and forming a saturated or supersaturated aqueous solution thereof,
(2) inoculating the aqueous solution with crystals of one optically active form of cysteine hydrochloride as seed crystals, and
(3) preferentially crystallizing optically the same form of the cysteine hydrochloride used as the seed crystals, in a state of a monohydrate thereof.

The crystals of optically active D- or L-cysteine hydrochloride used in step (2) for inoculation can be those present in excess amount in and crystallized from a supersaturated solution of a mixture thereof.

More specifically, it has been found that, when DL-cysteine is converted into crystals of DL-cysteine hydrochloride having a much higher solubility in water than the free form (see curve ① of the FIGURE), which are not substantially oxidized by dissolved oxygen. On the other hand, the L-form or D-form of cysteine hydrochloride has a fairly lower solubility in water than DL-cysteine hydrochloride (see curve ② of the FIGURE). Thus, it becomes possible to separate crystals of the L-form or D-form of cysteine hydrochloride from DL-cysteine hydrochloride using the inoculation process.

BRIEF DESCRIPTION OF THE ACCOMPANYING DRAWING

The FIGURE shows the solubility in water of free cysteine and cysteine hydrochloride in racemate and optically active forms, respectively.

DETAILED DESCRIPTION OF THE INVENTION

The present invention provides (1) a process for industrially providing D-cysteine inexpensively from a racemate after the L-form obtained from natural material has been racemized, and (2) a process for industrially providing L- or D-cysteine inexpensively from chemically synthesized DL-cysteine in the same manner as that for the natural materials. The process for racemization as described above can be any of (1) a process which comprises converting cysteine into cystine and then boiling such in a concentrated mineral acid (see E. Salkowski, *Biochem. Z.*, 131 1 (1922)), and (2) a process which comprises converting cysteine into cystine, adding a greatly excess amount of acetic anhydride for acetylation simultaneously with racemization, obtaining optically inactive cystine by deacetylation, and reducing cystine to obtain DL-cysteine, as desired. This acetylation is described in, for example, J. P. Greenstein et al., *J. Am. Chem. Soc.*, 79,4542 (1957). Further, DL-cysteine may be synthesized by any process. For example, these processes include (1) DL-cysteine synthesized from serine (see P. Rambacher, Ber., 101 2595 (1968)), (2) DL-cysteine synthesized by hydrolysis of thiazoline derivatives (see *Ann.*, 574 140 (1951)), and (3) DL-cysteine derived from $\beta$-chloroalanine (see E. M. Fry, *J. Org. Chem.*, 15 438 (1950) and Japanese Patent Application (OPI) No. 164669/80), etc. DL-cysteine hydrochloride can be easily produced. It can be obtained as crystals by dissolving DL-cysteine in an aqueous solution of hydrochloric acid in an amount of 1 mol or less, as hydrogen chloride, and concentrating the resulting solution.

The crystals are dried at 40° C. by warm air or washed with a mixture of ethanol-diethylether-hydrochloric acid (e.g., 1:1:0.2 by volume) and thereafter they are stored in a dry state.

Various approaches can be utilized for making a saturated or a supersaturated aqueous solution of the DL-cysteine hydrochloride. Although cooling and concentrating are the most common means, a process which comprises gradually dissolving to form a saturated solution of the DL-form at a high temperature may be utilized or the amount of hydrochloric acid added may be controlled.

Although the concentration of the DL-cysteine hydrochloride in the aqueous solution is not restricted, it is preferable to control the supersaturation in order to obtain a product having a higher optical purity. The solution, or mother liquor, after the resolution can be repeatedly reused by supplying additional DL-form.

Although the resolution temperature is not particularly limited, there is naturally a limitation, because the melting point of crystals of DL-cysteine hydrochloride is comparatively low. Preferably, the resolution is carried out at about 45° C. or less. However, in using a low temperature, it is preferred to carry the resolution out at about 10° C. or more, because the viscosity of the solution increases and the crystal growth rate becomes low.

The amount of crystals of optically active cysteine hydrochloride used in inoculation is not restricted. The resolution operation proceeds faster as the amount of crystals used for inoculation is increased, but it is preferred for the concentration of crystals used for inoculation be about 30% by weight or less so that uniform stirring of the solution can be carried out. It is sufficient that the inoculation is with crystals in an amount of about 0.5% by weight or more, if only a small amount is to be used. When the amount of crystals for inoculation is fixed at a certain value, the surface area of crystals increases as the particle size thereof decreases and, consequently, the crystal growth rate becomes high. Crystals of any particle size can be appropriately used, if they have a particle size which does not cause difficulties on filtration, drying or during operation. With crystals having a larger particle size, the same difficulties occur. More specifically, when the crystal particle size is too large, a large amount of crystals must be used in the inoculation because the surface area becomes small, and uniform stirring of the solution becomes difficult. Crystals having a particle size of 20 mesh (840 $\mu$m) to 200 mesh (74 $\mu$m) can be appropriately used.

Further, it is also possible in this invention to inoculate the solution with both crystals of optically active L-form and D-form of cysteine hydrochloride as seed crystals at the same time, and then to separate by filtration the resulting crystals of L-form and D-form, both being in a monohydrate state of cysteine hydrochloride, each of which has a different particle size (e.g., as disclosed in Japanese Patent Publication No. 9069/62 (corresponding to U.S. Pat. No. 2,898,358)). In the inoculation with the seed crystals, the crystals of L-form and D-form to be inoculated may be the same or different from each other in particle size. Further, it is preferable that the crystals of L-form and D-form to be inoculated are in a monohydrate state of cysteine hydrochloride.

As the method for inoculating both the L-form and D-form crystals at the same time, those as disclosed in Japanese Patent Publication Nos. 9971/62 and 17710/61 are applicable. According to the method as described in the former Japanese patent publication, the inoculation is carried out with crystals of both optically active forms of cysteine hydrochloride, whereby the crystals of each optically active form are suspended in a vessel equipped with a suspending machine through which a supersaturated racemate solution is circulated. On the other hand, according to the method as described in the latter Japanese patent publication, the inoculation is carried out by suspending the seed crystals in an ascending circulate supersaturated racemate solution current.

It is, of course, preferred for the optically active compound used for inoculation to have a high optical purity. However, optically impure compounds may be used, if desired.

Since the other optically active compound is present in an excess amount in the mother liquor after completion of the resolution process by the above-described operation, the resolution is carried out in the same manner by inoculating the solution with seed crystals for the form of the compound which is present in an excess amount in the solution with or without supplying the DL-form. In this case, it is possible to achieve resolution by crystallizing the active compound which is present in an excess amount in a supersaturated state, spontaneously, without inoculating the solution with seed crystals.

After the DL-cysteine hydrochloride is separated into the D-form and the L-form, an undesired form can be racemized using any known method into the DL-form and then recycled as a starting material for resolution.

According to the present invention, it is not necessary at all for the resulting optically active compound to be subjected to neutralization, an ion-exchange treatment, conversion into the free acid or exchange for another salt, etc., which is required in various known processes. Specifically, crystals of L-cysteine hydrochloride can be obtained directly in a condition suitable to meet food additive standards, by which the crystals can be utilized as the product as they are. If desired, the cysteine hydrochloride is easily converted into cysteine. For example, the desired cysteine can be obtained by a process which comprises removal of the hydrochloric acid in an organic solvent such as methanol or ethanol with a base such as triethylamine, etc., or a process which comprises neutralization in an aqueous solution with an action of a weak base such as lithium hydroxide, etc.

The present invention is illustrated in greater detail below by reference to typical examples thereof. However, these examples are given merely to facilitate an understanding of the present invention, and are not to be construed as limiting the present invention.

Unless otherwise indicated herein, all parts, percents, ratios and the like are by weight.

EXAMPLE 1

37 g of water was added to 128 g of crystals of DL-cysteine hydrochloride monohydrate. After the mixture was heated to 35° C. for complete dissolution, the solution was gradually cooled. When the temperature of the solution reached 31° C., the solution was inoculated with 1.0 g of crystals of L-cysteine hydrochloride monohydrate having a particle size of 40 to 60 mesh (250 to 350 μm), and a specific rotatory power of $[\alpha]_D^{20} = +6.30°$ (C: 8, N HCl). Thereafter, the solution was cooled to 27.5° C. over a 70 minute period with stirring. Then, 1.0 ml of the supernatant liquid was sampled and diluted with a 1N aqueous solution of hydrochloric acid to make 10 ml. When the optical rotation was measured, it was $[\alpha]_D^{20} = -0.016°$, by which it was ascertained that resolution had occurred. Then, the crystals which had grown were filtered off rapidly.

Thus, 5.4 g, on a dry weight basis, of crystals of L-cysteine hydrochloride monohydrate was obtained. The specific rotatory power was $[\alpha]_D^{20} = +5.67°$ (C: 8, N HCl). When this was compared with the specific rotatory power of pure L-cysteine hydrochloride monohydrate of $[\alpha]_D^{20} = +6.30°$, it was found to have an optical purity of 90.0%.

To the above described mother liquor after resolution, 4.0 g of crystals of DL-cysteine hydrochloride monohydrate was additionally added, and the solution was heated again to 35° C. After complete dissolution, the solution was gradually cooled. When the temperature reached 31+ C., the solution was inoculated with 1.0 g of crystals of D-cysteine hydrochloride monohydrate having a particle size of 100 to 120 mesh (125 to 149 μm) and a specific rotatory power of $[\alpha]_D^{20} = -6.30°$ (C: 8, N HCl) and thereafter the same procedure as described above was carried out. Thus, 8.0 g, on a dry weight basis, of crystals of D-cysteine hydrochloride monohydrate was obtained, which had a specific rotatory power of $[\alpha]_D^{20} = -5.04°$ (C: 8, N HCl) and an optical purity of 80%.

EXAMPLE 2

128 g of an aqueous solution containing 77.5% by weight of DL-cysteine hydrochloride monohydrate was cooled gradually from 35° C. When the temperature reached 30.5° C., the solution was inoculated with 1 g of crystals of L-cysteine hydrochloride monohydrate having a particle size of 60 to 80 mesh (117 to 250 μm) having a specific rotatory power of $[\alpha]_D^{20} = +6.30°$ (C: 8, N HCl) and the solution was cooled to 29° C. over a period of 100 minutes with stirring. The crystals which had grown were filtered off to obtain 2.0 g, on a dry weight basis, of L-cysteine hydrochloride monohydrate, which had a specific rotatory power of $[\alpha]_D^{20} = +6.30°$ (C: 8, N HCl) and an optical purity of 100%.

EXAMPLE 3

To crystals containing 128 g of DL-cysteine hydrochloride monohydrate and a 6 g of L-cysteine hydrochloride monohydrate, 37 g of water was added. After complete dissolution at 40° C., the solution was cooled at a rate of 1.0° C. per 10 minutes with stirring. When the temperature reached 29° C., formation of nuclei was observed. Cooling was stopped and the stirring was continued at 29° C. for 30 minutes. Crystallization was stopped by rapidly filtering the solution, by which 16.0 g, on a dry weight basis, of L-cysteine hydrochloride monohydrate was obtained. It had a specific rotatory power of $[\alpha]_D^{20} = +4.85°$ (C: 8, N HCl) and an optical purity of 77.0%.

COMPARATIVE EXAMPLE 11 g of DL-cysteine was added to 100 g of water. After complete dissolution with heating to 40° C., the solution was gradually cooled. When the temperature reached 31° C., the solution was inoculated with 0.5 g of L-cysteine having a specific rotatory power of $[\alpha]_D^{20} = +8.0°$ (C: 2, N HCl) with stirring, followed by cooling to 27° C. over 2 hours. The crystals which had grown were filtered off to obtain 2 g of crystals. When the optical rotation was measured, the separated crystals 1.5 g were all DL-cysteine. As a result of analysis, it was found that it contained 5% of cystine.

While the invention has been described in detail and with reference to specific embodiments thereof, it will be apparent to one skilled in the art that various changes and modifications can be made therein without departing from the spirit and scope thereof.

What is claimed is:

1. A process for the optical resolution of DL-cysteine which comprises
    (1) converting DL-cysteine into a hydrochloride thereof and forming a saturated or supersaturated aqueous solution thereof,
    (2) inoculating said solution with crystals of one optically active form of cysteine hydrochloride as seed crystals, and
    (3) preferentially crystallizing optically the same form of the cysteine hydrochloride used as the seed crystals, in a state of a monohydrate thereof.

2. The process of claim 1, wherein said seed crystals are optically active D- or L-cysteine hydrochloride monohydrate.

3. The process of claim 2, wherein said seed crystals are optically active D- or L-cysteine hydrochloride monohydrate produced by crystallization of that optically active form present in excess in a super-saturated solution thereof.

4. The process of claim 1, wherein said inoculation is with crystals of both optically active forms of cysteine hydrochloride as seed crystals, whereby crystals of each optically active form of cysteine hydrochloride monohydrate are crystallized.

5. The process of claim 4, wherein said seed crystals are both optically active D- and L-cysteine hydrochloride monohydrates.

* * * * *